United States Patent [19]

Matsumoto et al.

[11] Patent Number: 4,705,554
[45] Date of Patent: Nov. 10, 1987

[54] BENZOFURANYLOXYPHENYLUREA DERIVATIVE AND HERBICIDAL COMPOSITION CONTAINING IT AS AN ACTIVE INGREDIENT

[75] Inventors: Susumu Matsumoto; Shigeru Suzuki; Hisao Watanabe; Hiroshi Hanabe, all of Yokohama, Japan

[73] Assignee: Mitsubishi Chemical Industries Limited, Tokyo, Japan

[21] Appl. No.: 930,451

[22] Filed: Nov. 14, 1986

[30] Foreign Application Priority Data

Dec. 3, 1985 [JP] Japan ................... 60-272091

[51] Int. Cl.$^4$ .................. A01N 47/30; C07D 307/86; C07D 307/79
[52] U.S. Cl. .......................... 71/88; 549/462
[58] Field of Search ............. 549/462; 71/88

[56] References Cited

U.S. PATENT DOCUMENTS 3,119,682 1/1964 Martin et al. ................ 71/2.6
4,426,385 1/1974 Cain ........................... 546/323

FOREIGN PATENT DOCUMENTS 0036390 10/1983 European Pat. Off. .
0093610 11/1983 European Pat. Off. .
0105735 4/1984 European Pat. Off. .
3222974 12/1983 Fed. Rep. of Germany .
3418532 6/1985 Fed. Rep. of Germany .

OTHER PUBLICATIONS

Chemical Abstracts, vol. 97, No. 7, Aug. 16, 1982, Columbus, Ohio, USA—Sumitomo Chemical Co., Ltd. "Urea Derivatives" p. 618, col. 1, Abstract No. 55 502y & Jpn. Kokai Tokkyo Koho JP 82 04,962, Jan. 1982.

Primary Examiner—Henry R. Jiles
Assistant Examiner—Bernard I. Dentz
Attorney, Agent, or Firm—Oblon, Fisher, Spivak, McClelland & Maier

[57] ABSTRACT

A benzofuranyloxyphenylurea derivative having the formula:

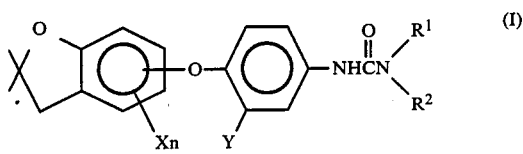

wherein X is a halogen atom or a trifluoromethyl group, n is an integer of from 0 to 2, Y is a hydrogen atom, a halogen atom or a trifluoromethyl group, $R^1$ is a lower alkyl group, and $R^2$ is a lower alkyl group, a lower alkenyl group, a lower alkynyl group or a lower alkoxy group. The compounds are useful as herbicides.

14 Claims, No Drawings

BENZOFURANYLOXYPHENYLUREA DERIVATIVE AND HERBICIDAL COMPOSITION CONTAINING IT AS AN ACTIVE INGREDIENT

The present invention relates to a benzofuranyloxyphenylurea derivative and a herbicidal composition containing the derivative as an active ingredient.

Heretofore, certain phenoxyphenylurea derivatives have been known to have herbicidal activities. For instance, U.S. Pat. No. 3,119,682 discloses a herbicide containing a compound of the formula:

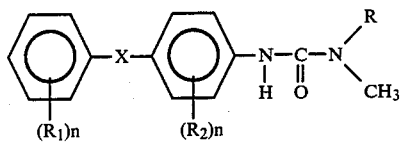

wherein R is a lower alkyl group, each of $R_1$ and $R_2$ is selected from the group consisting of a hydrogen atom, a halogen atom, a lower alkyl group, a trifluoromethyl group, a lower alkoxy group and a nitro group, X is selected from the group consisting of O and S, and n is an integer of at most 3. However, it is difficult to foresee the herbicidal activities or selectivity of a new compound from a mere similarity of the chemical structure to such known compounds, since in many cases, a slight modification in the structure of a chemical substance results in a substantial difference in the presence or absence of the effectiveness of the herbicidal activities, or in the selectivity.

On the other hand, U.S. Pat. No. 4,426,385 discloses that certain bicyclooxyphenylurea derivatives have insecticidal activities. As a compound having a benzofuranyloxyphenylurea moiety, 3-(3-chloro-4-[2,3-dihydro-2,2-dimethyl-7-benzofuranyloxy]phenyl)-1-(2,6-difluorobenzoyl)urea is disclosed. The bicyclooxyphenylurea derivatives disclosed in U.S. Pat. No. 4,426,385 are known to have insecticidal activities, but nothing is known about the herbicidal activities of such derivatives.

It is an object of the present invention to provide a novel benzofuranyloxyphenylurea derivative having excellent herbicidal activities.

The present invention provides a benzofuranyloxyphenylurea derivative having the formula:

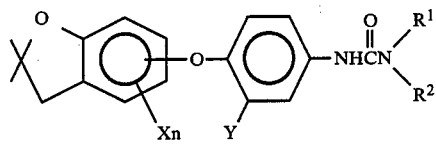

wherein X is a halogen atom or a trifluoromethyl group, n is an integer of from 0 to 2, Y is a hydrogen atom, a halogen atom or a trifluoromethyl group, $R^1$ is a lower alkyl group, and $R^2$ is a lower alkyl group, a lower alkenyl group, a lower alkynyl group or a lower alkoxy group.

The present invention also provides a herbicidal composition comprising a herbicidally effective amount of the derivative of the formula I as an active ingredient and a carrier.

Now, the present invention will be described in detail with reference to the preferred embodiments.

In the present invention, the compound used as the active ingredient of a herbicidal composition, is represented by the formula I.

In the formula I, the halogen atom includes a fluorine atom, a chlorine atom, a bromine atom and an iodine atom, and the lower alkyl or lower alkoxy group includes an alkyl or alkoxy group having from 1 to 4 carbon atoms, respectively. Likewise, the lower alkenyl or lower alkynyl group includes an alkenyl or alkynyl group having from 2 to 4 carbon atoms, respectively.

It is preferred that X is a fluorine atom, a chlorine atom, a bromine atom or a trifluoromethyl group, n is an integer of from 0 to 2, Y is a hydrogen atom, a fluorine atom, a chlorine atom, a bromine atom or a trifluoromethyl group, $R^1$ is an alkyl group having from 1 to 3 carbon atoms, and $R^2$ is an alkyl group having from 1 to 3 carbon atoms, an allyl group, a propargyl group or an alkoxy group having from 1 to 3 carbon atoms.

When the herbicidal activities are taken into account, it is particularly preferred that X is a fluorine atom, a chlorine atom, a bromine atom or a trifluoromethyl group, n is an integer of 0 or 1, Y is a hydrogen atom, a fluorine atom, a chlorine atom, a bromine atom or a trifluoromethyl group, $R^1$ is a methyl group, and $R^2$ is a methyl group or a methoxy group respectively.

The compounds of the formula I of the present invention are novel compounds, which may be prepared, for instance, by the following reactions by using various starting materials.

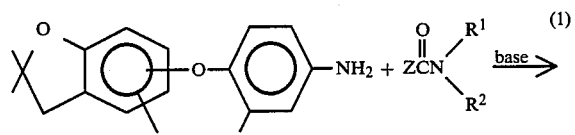

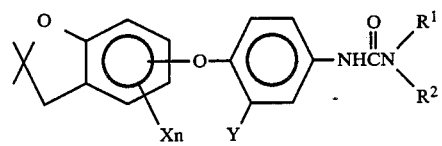

In the above reaction formulas, X, Y, $R^1$, $R^2$ and n are as defined above, and Z is a halogen atom.

The above reaction is conducted in the presence of an organic base such as triethylamine, pyridine or N,N-diethylaniline, or an inorganic base such as sodium carbonate or sodium hydroxide in a solvent, for example, a ketone such as acetone or ethyl methyl ketone, an aromatic hydrocarbon such as benzene or toluene, an ether such as diethyl ether or tetrahydrofuran, or an aprotic polar solvent such as acetonitrile, N,N-dimethylformamide, dimethylsulfoxide or N-methylpyrrolidone, or in the absence of a solvent, at a temperature within a range of from 0° to 150° C.

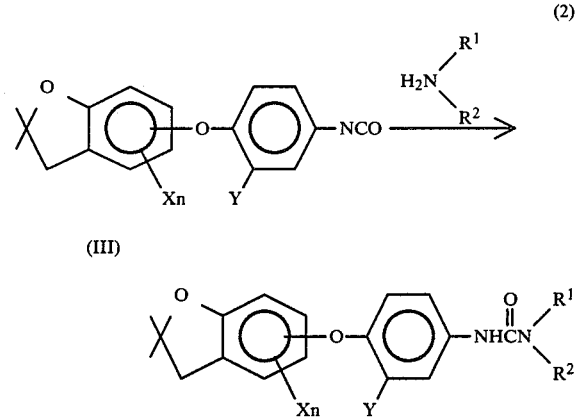

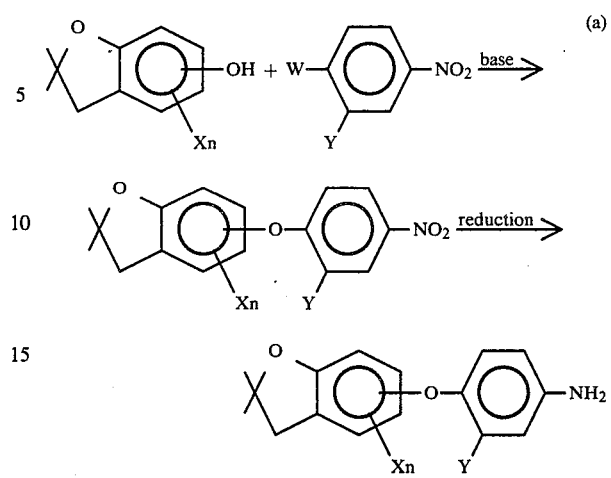

In the above reaction formulas, X, Y, R¹, R² and n are as defined above.

The above reaction is conducted in the absence of a solvent, or in a solvent, for example, an aromatic hydrocarbon such as benzene, toluene, xylene or chlorobenzene, an acetic acid ester such as ethyl acetate or isobutyl acetate, an ether such as diethyl ether, diisopropyl ether, tetrahydrofuran or dioxane, an aprotic polar solvent such as N,N-dimethylformamide, dimethylsulfoxide or N-methylpyrrolidone, a ketone such as acetone or ethyl methyl ketone, an alcohol such as methanol, ethanol, isopropanol or butanol, or water or in a mixture of such solvents, at a temperature within a range of from −50° to 100° C.

The isocyanate of the formula III used as the starting material in the above reaction, can be prepared by the following reaction from the aniline of the formula II used as a starting material in the above reaction (1).

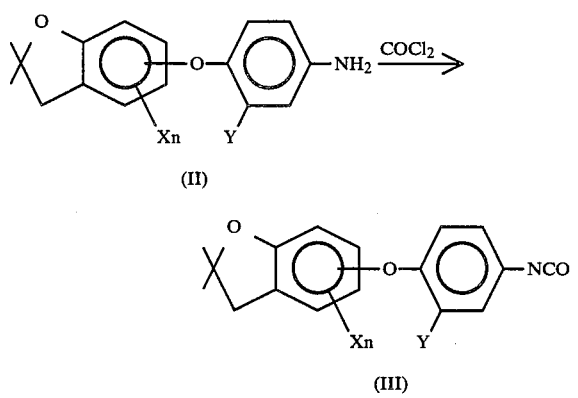

In the above reaction formulas, X, Y and n are as defined above.

The above reaction is conducted in a solvent, for example, an aromatic hydrocarbon such as benzene, toluene, xylene or chlorobenzene, an acetic acid ester such as ethyl acetate or isobutyl acetate, or an ether such as diethyl ether, diisopropyl ether, tetrahydrofuran or dioxane, in the presence or absence of an organic base such as triethylamine, pyridine, quinoline or N,N-diethylaniline, at a temperature within a range of from −20° to 180°.

The aniline derivative of the formula II used as the starting material for the reactions (1) and (2), can be prepared by the following process (a) or (b).

In the above reaction formulas, X, Y and n are as defined above, and W is a halogen atom.

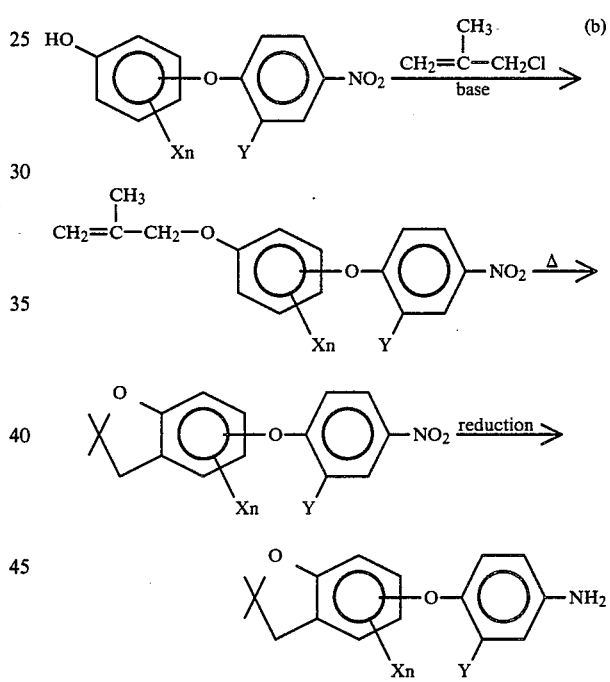

In the above reaction formulas, X, Y and n are as defined above.

The compounds of the present invention thus prepared, may be used by themselves as herbicides. Usually, however, they are used in the form of an emulsion, a dust, granules, a wettable powder or the like, in admixture with an inert liquid carrier or solid carrier with a further addition of a suitable surfactant.

As the liquid carrier, there may be mentioned toluene, xylene, methylnaphthalene, cyclohexane, butanol, glycol, dimethylsulfoxide, dimethylformamide, acetone, methyl isobutyl ketone, an animal or vegetable oil, a fatty acid, a fatty acid ester or water. Likewise, as the solid carrier, there may be mentioned clays, kaolin clay, talc, bentonite, diatomaceous earth, silica, calcium carbonate or a vegetable powder such as a soybean powder or a wheat powder. Further, if necessary, other active components such as agricultural fungicides, insecticides, nematocides or other herbicides, plant growth controlling agents, soil improvers or fertilizers, may also be incorporated. Moreover, to ensure the herbicidal effects, a proper adjuvant such as an extender, an emulsifier, a wetting agent or a fixing agent may optionally be incorporated.

The amount of application (i.e. the dose) of the herbicidal composition of the present invention varies depending upon the type of the compound, the weeds to be killed, the season for the treatment, the manner for the treatment or the nature of the soil. However, it is usually within a range of from 0.5 to 80 g/are, preferably from 1 to 50 g/are, as the active ingredient.

The herbicidal compositions containing the compounds of the present invention as active ingredients are capable of controlling weeds in upland fields, such as lambsquarters (*Chenopodium album*), goosefoot (*Chenopodium album* var. *centrorubrum*), persicaria blumei gross (*Polygonum blumei*), ladysthumb (*Polygonum persicaria*), livid amaranth (*Amaranthus lividus*), common purselane (*Portulaca oleracea*), common chickweed (*Stellaria media*), dead-nettle (*Lamium amplexicaule*), large crabgrass (*Digitaria sanguinalis*), goosegrass (*Eleusine indica*), green foxtail (*Setaria viridis*), water foxtail (*Alopecurus aequalis*) and flat-sedge (*Cyperus microiria*) and weeds in paddy fields, such as false pimpernel (*Lindernia procumbens*), toothcup (*Rotala indica*), abunome (*Dopatrium junceum*), american waterwort (*Elatine triandra*), narrowleaf waterplantain (*Alisma canaliculatum*), barnyardgrass (*Echinochloa crus-galli L. Beauv.* var. *crus-galli*), umbrella plant (*Cyperus difformis*) and duck-tongue weed (*Monochloria vaginalis*) by the preemergence treatment or by the treatment during the growing stage. Further, the compounds of the present invention can be used as selective herbicides for the cultivation of crop plants such as rice (*Oryza sative*), sunflower (*Helianthus annuus*), potato (*Salanum tuberosum*), wheat (*Triticum aestivum*), barley (*Hordeum vulgare*), sugar cane (*Saccharum officinarum*), and corn (*Zea mays*).

Thus, the compounds of the present invention have excellent properties such that they are capable of controlling a number of weeds without substantially adversely affecting the crop plants.

Further, the compounds of the present invention exhibit high herbicidal activities against the weeds which used to be hardly controlled by conventional herbicides, such as velvetleaf (*Abutilon theophrasti*), purple-flowered thornapple (*Datura tatula L.*), wild mustard (*Brassica kaber* var. *pinnatifida*), bedstraw (*Galium aparine*), western violet (*Viola* sp.), and pineappleweed (*Matricaria matricarioides*), in upland fields. Thus, the compounds of the present invention have a very wide herbicidal spectrum and at the same time a high level of safety.

The scope of application of the compounds of the present invention is not limited to the above-mentioned types of plants, and the compounds of the present invention are useful also to other plants by a similar manner of application.

Now, the present invention will be described in further detail with reference to Examples. However, it should be understood that the present invention is by no means restricted to such specific Examples.

EXAMPLE 1

1-[4-(2,3-dihydro-2,2-dimethyl-5-benzofuranyloxy)-phenyl]-3-methoxy-3-methylurea 6.5 g of 4-(2,3-dihydro-2,2-dimethyl-5-benzofuranyloxy)aniline was dissolved in 30 ml of pyridine, and 3.8 g of N-methoxy-N-methylcarbamoyl chloride was gradually dropwise added thereto over a period of 30 minutes under cooling with ice. Stirring was continued for 1.5 hours, and then pyridine was distilled off under reduced pressure. The residual oily substance was dissolved in 100 ml of toluene, and washed sequentially with water, a dilute hydrochloric acid aqueous solution and a saturated sodium chloride aqueous solution. Then, toluene was distilled off. The residue was purified by silica gel column chromatography by using a solvent mixture of ethyl acetate/n-hexane=$\frac{1}{3}$ as the developer, to obtain 7.5 g of compound No. 19 as identified in Table 1.

EXAMPLE 2

1-[4-(2,3-dihydro-2,2-dimethyl-7-benzofuranyloxy)-phenyl]-3-methoxy-3-methylurea 1.5 g of 4-(2,3-dihydro-2,2-dimethyl-7-benzofuranyloxy)aniline was dissolved in 20 ml of N,N-dimethylformamide, and 0.8 g of N-methoxy-N-methylcarbamoyl chloride was gradually added to this solution at room temperature. After 1.5 hours, N,N-dimethylformamide was distilled off under reduced pressure. The residue was dissolved in ethyl acetate, washed with water and dried over magnesium sulfate. After distilling off the solvent, the residual oily substance was purified by silica gel column chromatography by using a solvent mixture of ethyl acetate/n-hexane=$\frac{1}{4}$ as the developer, to obtain 1.4 g of compound No. 2 as identified in Table 1.

EXAMPLE 3

1-[4-(2,3-dihydro-2,2-dimethyl-5-benzofuranyloxy)-phenyl]-3-ethoxy-3-methylurea 1.8 g of 4-(2,3-dihydro-2,2-dimethyl-5-benzofuranyloxy)phenyl isocyanate was dissolved in 20 ml of toluene, and 2.0 g of N-methyl-O-ethylhydroxylamine dissolved in 5 ml of toluene, was dropwise added thereto over a period of 20 minutes at room temperature. The mixture was stirred at room temperature for 2 hours, and then the solvent was distilled off. The residue was purified by silica gel column chromatography by using a solvent mixture of ethyl acetate/n-hexane=$\frac{1}{4}$ as the developer, to obtain 2.2 g of compound No. 29 as identified in Table 1.

In the same manner as above, compounds identified in Table 1 were prepared. The melting point or refractive index of each compound is also shown in Table 1.

TABLE 1

[Structure: bicyclic benzofuran-O-phenyl(Y)-NHC(=O)N(R¹)(R²) with Xn substituent]

[Xn group structure: 2,2-dimethyl-2,3-dihydrobenzofuran with O— linkage]

| No. | Xn | Y | R¹ | R² | Melting point or refractive index |
|---|---|---|---|---|---|
| 1 | 2,2-dimethyl-2,3-dihydrobenzofuran-7-yloxy | H | CH₃ | CH₃ | 160–161° C. |
| 2 | " | " | " | OCH₃ | 103–104° C. |
| 3 | " | F | " | CH₃ | 144–145° C. |
| 4 | " | " | " | OCH₃ | 98.5–99.5° C. |
| 5 | 4-fluoro-2,2-dimethyl-2,3-dihydrobenzofuran-7-yloxy | H | " | CH₃ | 135–136° C. |
| 6 | " | " | " | OCH₃ | 116–117° C. |
| 7 | 4-chloro-2,2-dimethyl-2,3-dihydrobenzofuran-7-yloxy | " | " | CH₃ | 153.0–153.5° C. |
| 8 | " | " | " | OCH₃ | 89–90.5° C. |
| 9 | " | Cl | " | CH₃ | 158.5–159.5° C. |
| 10 | 5-chloro-2,2-dimethyl-2,3-dihydrobenzofuran-7-yloxy | H | " | " | 158–160° C. |
| 11 | " | " | " | OCH₃ | 98.5–99.5° C. |
| 12 | 4-bromo-2,2-dimethyl-2,3-dihydrobenzofuran-7-yloxy | " | " | CH₃ | 129.0–129.5° C. |
| 13 | " | " | " | OCH₃ | 108–109° C. |

TABLE 1-continued
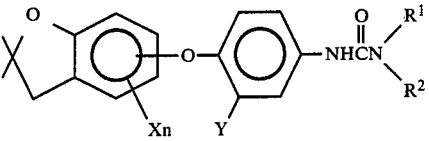
| No. | Xn | Y | R¹ | R² | Melting point or refractive index |
|---|---|---|---|---|---|
| 14 | | " | " | CH₃ | 159–161° C. |
| 15 | | " | " | " | 180.5–181.5° C. |
| 16 | | " | " | " | 190–191° C. |
| 17 | | " | " | OCH₃ | $n_D^{25}$ 1.5625 |
| 18 | | " | " | CH₃ | 154–155° C. |
| 19 | " | " | " | OCH₃ | 95–96° C. |
| 20 | " | F | " | CH₃ | 167–168° C. |
| 21 | " | " | " | OCH₃ | 107–108° C. |
| 22 | " | Cl | " | " | 96–97° C. |
| 23 | " | CF₃ | " | " | amorphous |
| 24 | | H | " | " | 115.5–116.5° C. |

TABLE 1-continued

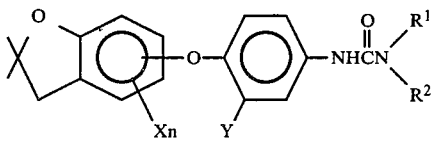

| No. | Xn | Y | R[1] | R[2] | Melting point or refractive index |
|---|---|---|---|---|---|
| 25 | (structure with Cl) | " | " | " | 106–107° C. |
| 26 | (structure with Br) | " | " | CH₃ | 203–204° C. |
| 27 | " | " | " | OCH₃ | 105–106° C. |
| 28 | (structure) | " | C₂H₅ | C₂H₅ | 131–132° C. |
| 29 | " | " | CH₃ | OC₂H₅ | 97–98° C. |
| 30 | " | " | " | CH₂CH=CH₂ | 120–121° C. |
| 31 | " | " | " | CH₂C≡CH | 117.5–118.5° C. |
| 32 | (structure) | " | " | OCH₃ | $n_D^{25}$ 1.5743 |

Now, Formulation Examples of the compounds of the present invention will be presented. In the following Examples, "parts" and "%" mean "parts by weight" and "% by weight", respectively.

FORMULATION EXAMPLE 1

Wettable Powder

40 Parts of a compound of the present invention as identified in Table 1, 20 parts of Carplex #80 (trade name, Shionogi & Co., Ltd.), 35 parts of N,N-kaolin clay (trade mark, Tsuchiya Kaolin Co., Ltd.) and 5 parts of a higher alcohol sulfuric acid ester surfactant, Sorpol 8070 (trade mark, Toho Chemical Co., Ltd.) were uniformly mixed and pulverized to obtain a wettable powder containing 40% of the active ingredient.

FORMULATION EXAMPLE 2

Granules

1 Part of a compound of the present invention as identified in Table 1, 43 parts of clay (manufactured by Nippon Talc Co., Ltd.), 55 parts of bentonite (manufactured by Hojunyoko Co., Ltd) and 1 part of succinate surfactant Airol CT-1 (trade mark, Toho Chemical Co., Ltd.) were mixed and pulverized, and 20 parts of water was added thereto. The mixture was kneaded. The mixture was extruded from an orifice having a diameter of 0.6 mm by using an extrusion type granulator. The extruded material was dried at 60° C. for 2 hours, and then cut into a length of from 1 to 2 mm to obtain granules containing 1% of the active ingredient.

FORMULATION EXAMPLE 3

Emulsion

30 Parts of a compound of the present invention as identified in Table 1 was dissolved in a solvent mixture comprising 30 parts of xylene and 25 parts of dimethylformamide, and 15 parts of a polyoxyethylene surfactant, Sorpol 3005X (trade mark, Toho Chemical Co., Ltd.) was added thereto to obtain an emulsion containing 30% of the active ingredient.

FORMULATION EXAMPLE 4

Flowable Agent

30 Parts of a compound of the present invention as identified in Table 1 was thoroughly mixed and dispersed in a preliminarily prepared mixture of 8 parts of ethylene glycol, 5 parts of Sorpol AC3032 (trade mark, Toho Chemical Co., Ltd.), 0.1 part of xanthane gum and 56.9 parts of water. Then, this slurry mixture was wet-pulverized in a Dinomil (manufactured by Symmal Enterprizes Co.) to obtain a stable flowable agent containing 30% of the active ingredient.

Now, Test Examples of the compounds of the present invention will be presented.

TEST EXAMPLE 1

Flooded Soil Treatment Test

A resin vat of 1/2,500 are was filled with paddy diluvium soil and manured. A suitable amount of water was added thereto, and puddling was conducted. Then, seeds of barnyardgrass, spike-flowered rotala and monochoria were sown in a depth of 0.5 cm in the soil.

On the other hand, two rice plants each consisting three rice seedlings of 2 or 3 leaf stage (variety: Akinishiki, quality of the seedlings: good) were transplanted to the vat in a depth of about 1 cm. Then, the water level was maintained at a depth of about 3.5 cm, and on the third day after the transplantation, granules containing a compound of the present invention as the active ingredient, prepared in accordance with the Formulation Example 2, or granules containing a comparative compound 1-[4-(4-chlorophenoxy)phenyl]-3,3-dimethylurea as the active ingredient, prepared in the same manner as in Formulation Example 2, were scattered on the flooded surface in an amount to bring the dose of the active ingredient to 10 or 5 g/are. For 2 days after the treatment, a leaching loss of water was adjusted at a rate of 3 cm/day, and thereafter, the vat was kept in a greenhouse. On the 21st day after the treatment, the herbicidal effects and phytotoxicity were examined.

The results are shown in Table 2. The herbicidal effects were rated by the following equation and ratings.

$$\left(1 - \frac{\text{Survival terrestrial weed weight in treated area}}{\text{Survival terrestrial weed in non-treated area}}\right) \times 100 = Y\ (\%)$$

| Herbicidal effect rating | Y (%) |
| --- | --- |
| 0 | 0–5 |
| 1 | 6–30 |
| 2 | 31–50 |
| 3 | 51–70 |
| 4 | 71–90 |
| 5 | 91–100 |

Likewise, the phytotoxicities were rated by the following equation and ratings.

$$\left(1 - \frac{\text{Survival terrestrial crop plant weight in treated area}}{\text{Survival terrestrial crop plant weight in non-treated area}}\right) \times 100 = Y'\ (\%)$$

| Phytotoxicity rating | Y' (%) |
| --- | --- |
| 0 | 0–5 |
| 1 | 6–10 |
| 2 | 11–20 |
| 3 | 21–40 |
| 4 | 41–60 |
| 5 | 61–100 |

TABLE 2

Results of flooded soil treatment test

| Compound No. | Dose g/are | Herbicidal effect rating Barnyard-grass | Tooth-cup | Duck-tongue weed | Phytotoxicity rating Rice |
| --- | --- | --- | --- | --- | --- |
| 1 | 10 | 3 | 4 | 5 | 0 |
|  | 5 | 2 | 4 | 4 | 0 |
| 7 | 10 | 4 | 4 | 5 | 1 |
| 8 | 10 | 5 | 5 | 4 | 1 |
|  | 5 | 4 | 5 | 3 | 0 |
| 14 | 10 | 3 | 4 | 5 | 0 |
| 15 | 10 | 5 | 3 | 5 | 1 |
|  | 5 | 4 | 3 | 5 | 0 |
| 18 | 10 | 5 | 5 | 5 | 1 |
|  | 5 | 4 | 5 | 5 | 0 |
| 19 | 10 | 5 | 5 | 5 | 2 |
|  | 5 | 4 | 5 | 5 | 0 |
| 22 | 10 | 5 | 4 | 5 | 0 |
| 23 | 10 | 5 | 5 | 5 | 0 |
|  | 5 | 3 | 4 | 5 | 0 |
| 24 | 10 | 4 | 4 | 5 | 0 |
| 30 | 10 | 4 | 5 | 5 | 0 |
|  | 5 | 3 | 5 | 5 | 0 |
| Comparative compound | 10 | 3 | 1 | 3 | 3 |
|  | 5 | 2 | 0 | 2 | 1 |

TEST EXAMPLE 2

Foliage Treatment Test

Small size polyethylene pots of 1/8,850 are were filled with black volcano ash soil and manured, and then seeds of persicaria blumei gross, lambsquarters, velvetleaf, dead-nettle, bedstraw, corn and barley were sown in the pots, respectively.

The pots were kept in a greenhouse. When persicaria blumei gross reached 2 leaf stage, lambsquarters reached 3 leaf stage, velvetleaf reached 2 leaf stage, dead-nettle reached 2 leaf stage, bedstraw reached 1.5 leaf stage, corn reached 3 leaf stage and barley reached 2 leaf stage, a solution prepared by diluting a wettable powder containing a compound of the present invention as the active ingredient, prepared in Formulation Example 1, or a wettable powder containing a comparative compound 1-[4-(4-chlorophenoxy)phenyl]-3,3-dimethylurea as the active ingredient, prepared in the same manner as in Formulation Example 1, with water to bring the concentration of the active ingredient to 20, 10, 5 or 2.5 g/are, was sprayed at a rate of 10 liters per are by a small power pressurized sprayer. Then, each pot was kept and observed in a greenhouse. On the 15th day after the application of the herbicide, the herbicidal effects and the phytotoxicities were examined.

The results are shown in Table 3. The herbicidal effects and phytotoxicity were evaluated in accordance with the same standards as in Test Example 1.

TABLE 3

| Compound No. | Dose g/are | Persicaria blumei gross | Lambsquarters | Velvetleaf | Dead-nettle | Bedstraw | Corn | Barley |
|---|---|---|---|---|---|---|---|---|
| 2 | 10 | 5 | 5 | 4 | 5 | 4 | 0 | 0 |
|   | 5  | 4 | 5 | 3 | 5 | 3 | 0 | 0 |
| 3 | 10 | 4 | 4 | 4 | 4 | 3 | 0 | 0 |
| 4 | 10 | 4 | 5 | 4 | 5 | 4 | 0 | 0 |
| 5 | 10 | 5 | 5 | 4 | 5 | 4 | 0 | 0 |
| 6 | 10 | 5 | 5 | 5 | 5 | 4 | 0 | 1 |
| 7 | 10 | 5 | 5 | 5 | 5 | 5 | 0 | 1 |
|   | 5  | 5 | 5 | 4 | 5 | 4 | 0 | 0 |
|   | 2.5| 4 | 5 | 3 | 4 | 4 | 0 | 0 |
| 8 | 10 | 5 | 5 | 5 | 5 | 5 | 1 | 1 |
|   | 5  | 5 | 5 | 4 | 5 | 4 | 1 | 0 |
| 9 | 10 | 4 | 5 | 3 | 5 | 3 | 0 | 0 |
| 10| 10 | 5 | 5 | 4 | 5 | 3 | 1 | 1 |
| 11| 10 | 5 | 5 | 5 | 5 | 4 | 1 | 2 |
| 12| 10 | 5 | 5 | 4 | 5 | 4 | 0 | 1 |
| 13| 10 | 5 | 5 | 5 | 5 | 4 | 1 | 1 |
| 14| 10 | 5 | 5 | 4 | 5 | 4 | 0 | 1 |
|   | 5  | 4 | 4 | 3 | 4 | 2 | 0 | 0 |
| 15| 20 | 4 | 5 | 3 | 4 | 3 | 0 | 0 |
| 16| 10 | 5 | 5 | 5 | 5 | 5 | 1 | 1 |
|   | 5  | 4 | 5 | 4 | 5 | 4 | 0 | 0 |
| 17| 10 | 4 | 5 | 3 | 5 | 3 | 0 | 0 |
| 18| 10 | 5 | 5 | 5 | 5 | 5 | 0 | 0 |
|   | 5  | 5 | 5 | 4 | 5 | 5 | 0 | 0 |
| 19| 10 | 5 | 5 | 5 | 5 | 5 | 1 | 0 |
|   | 5  | 5 | 5 | 5 | 5 | 5 | 0 | 0 |
|   | 2.5| 5 | 5 | 3 | 5 | 4 | 0 | 0 |
| 20| 10 | 4 | 5 | 4 | 4 | 4 | 0 | 0 |
| 21| 10 | 4 | 5 | 4 | 5 | 4 | 0 | 1 |
| 22| 10 | 5 | 5 | 4 | 5 | 4 | 0 | 0 |
|   | 5  | 4 | 5 | 3 | 5 | 3 | 0 | 0 |
| 23| 10 | 5 | 5 | 4 | 4 | 4 | 0 | 0 |
|   | 5  | 4 | 4 | 3 | 4 | 2 | 0 | 0 |
| 24| 10 | 5 | 5 | 5 | 5 | 3 | 0 | 0 |
| 25| 10 | 5 | 5 | 3 | 4 | 4 | 0 | 0 |
| 26| 10 | 4 | 5 | 4 | 4 | 4 | 0 | 0 |
| 27| 10 | 5 | 5 | 4 | 5 | 4 | 0 | 1 |
| 28| 10 | 5 | 4 | 4 | 5 | 4 | 0 | 0 |
| 29| 10 | 5 | 5 | 5 | 5 | 3 | 0 | 0 |
| 30| 10 | 5 | 5 | 5 | 5 | 4 | 0 | 1 |
|   | 5  | 5 | 4 | 4 | 5 | 3 | 0 | 0 |
| 31| 10 | 5 | 5 | 4 | 5 | 3 | 0 | 0 |
| 32| 10 | 5 | 5 | 5 | 5 | 5 | 0 | 0 |
|   | 5  | 5 | 4 | 5 | 5 | 4 | 0 | 0 |
| Comparative compound | 10 | 4 | 4 | 2 | 4 | 2 | 2 | 3 |
|   | 5  | 2 | 2 | 1 | 2 | 0 | 1 | 2 |

We claim:

1. A benzofuranyloxyphenylurea derivative having the formula:

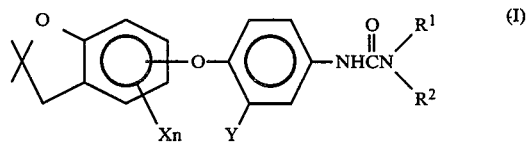

wherein X is a halogen atom or a trifluoromethyl group, n is an integer of from 0 to 2, Y is a hydrogen atom, a halogen atom or a trifluoromethyl group, $R^1$ is a lower alkyl group, and $R^2$ is a lower alkyl group, a lower alkenyl group, a lower alkynyl group or a lower alkoxy group.

2. The benzofuranyloxyphenylurea derivative according to claim 1, wherein in the formula I, X is a fluorine atom, a chlorine atom, a bromine atom or a trifluoromethyl group, n is an integer of from 0 to 2, Y is a hydrogen atom, a fluorine atom, a chlorine atom, a bromine atom, an iodine atom or a trifluoromethyl group, $R^1$ is a straight chain or branched alkyl group having from 1 to 4 carbon atoms, and $R^2$ is a straight chain or branched alkyl group having from 1 to 4 carbon atoms, an alkenyl group having from 2 to 4 carbon atoms, an alkynyl group having from 2 to 4 carbon atoms or an alkoxy group having from 1 to 4 carbon atoms.

3. The benzofuranyloxyphenylurea derivative according to claim 1, wherein in the formula I, X is a fluorine atom, a chlorine atom, a bromine atom or a trifluoromethyl group, n is an integer of from 0 to 2, Y is a hydrogen atom, a fluorine atom, a chlorine atom, a bromine atom or a trifluoromethyl group, $R^1$ is an alkyl group having from 1 to 3 carbon atoms, and $R^2$ is an alkyl group having from 1 to 3 carbon atoms, an allyl group, a propargyl group or an alkoxy group having from 1 to 3 carbon atoms.

4. The benzofuranyloxyphenylurea derivative according to claim 3, wherein in the formula I, X is a fluorine atom, a chlorine atom, a bromine atom or a trifluoromethyl group and n is an integer of 0 or 1.

5. The benzofuranyloxyphenylurea derivative according to claim 3, wherein in the formula I, R¹ is a methyl group.

6. The benzofuranyloxyphenylurea derivative according to claim 3, wherein in the formula I, R² is a methyl group or a methoxy group.

7. The benzofuranyloxyphenylurea derivative according to claim 1, wherein in the formula I, X is a fluorine atom, a chlorine atom or a trifluoromethyl group, n is an integer of 0 or 1, R¹ is a methyl group, and R² is a methyl group or a methoxy group.

8. A herbicidal composition comprising a herbicidally effective amount of the benzofuranyloxyphenylurea derivative having the formula:

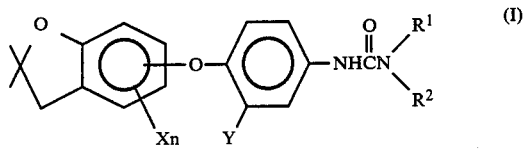

(I)

wherein X is a halogen atom or a trifluoromethyl group, n is an integer of from 0 to 2, Y is a hydrogen atom, a halogen atom or a trifluoromethyl group, R¹ is a lower alkyl group, and R² is a lower alkyl group, a lower alkenyl group, a lower alkynyl group or a lower alkoxy group, as an active ingredient and an inert carrier.

9. The herbicidal composition according to claim 8, wherein in the formula I, X is a fluorine atom, a chlorine atom, a bromine atom or a trifluoromethyl group, n is an integer of from 0 to 2, Y is a hydrogen atom, a fluorine atom, a chlorine atom, a bromine atom, an iodine atom or a trifluoromethyl group, R¹ is a straight chain or branched alkyl group having from 1 to 4 carbon atoms, and R² is a straight chain or branched alkyl group having from 1 to 4 carbon atoms, an alkenyl group having from 2 to 4 carbon atoms, an alkynyl group having from 2 to 4 carbon atoms or an alkoxy group having from 1 to 4 carbon atoms.

10. The herbicidal composition according to claim 8, wherein in the formula I, X is a fluorine atom, a chlorine atom, a bromine atom or a trifluoromethyl group, n is an integer of from 0 to 2, Y is a hydrogen atom, a fluorine atom, a chlorine atom, a bromine atom or a trifluoromethyl group, R¹ is an alkyl group having from 1 to 3 carbon atoms, and R² is an alkyl group having from 1 to 3 carbon atoms, an allyl group, a propargyl group or an alkoxy group having from 1 to 3 carbon atoms.

11. The herbicidal composition according to claim 10, wherein in the formula I, X is a fluorine atom, a chlorine atom, a bromine atom or a trifluoromethyl group and n is an integer of 0 or 1.

12. The herbicidal composition according to claim 10, wherein in the formula I, R¹ is a methyl group.

13. The herbicidal composition according to claim 10, wherein in the formula I, R² is a methyl group or a methoxy group.

14. The herbicidal composition according to claim 8, wherein in the formula I, X is a fluorine atom, a chlorine atom or a trifluoromethyl group, n is an integer of 0 or 1, R¹ is a methyl group, and R² is a methyl group or a methoxy group.

* * * * *